US009301809B2

(12) United States Patent
Douglas et al.

(10) Patent No.: US 9,301,809 B2
(45) Date of Patent: Apr. 5, 2016

(54) PRECISION EXTERNAL CONTROL OF INTERVENTIONAL MEDICAL PROCEDURES

(71) Applicants: David Byron Douglas, Winter Park, FL (US); Robert Edwin Douglas, Winter Park, FL (US); Kathleen Mary Douglas, Winter Park, FL (US)

(72) Inventors: David Byron Douglas, Winter Park, FL (US); Robert Edwin Douglas, Winter Park, FL (US); Kathleen Mary Douglas, Winter Park, FL (US)

( * ) Notice: Subject to any disclaimer, the term of this patent is extended or adjusted under 35 U.S.C. 154(b) by 222 days.

(21) Appl. No.: 13/953,897

(22) Filed: Jul. 30, 2013

(65) Prior Publication Data

US 2014/0039516 A1    Feb. 6, 2014

Related U.S. Application Data

(60) Provisional application No. 61/742,246, filed on Aug. 3, 2012.

(51) Int. Cl.
    *A61B 5/00*     (2006.01)
    *A61B 19/00*    (2006.01)
    *A61M 25/09*    (2006.01)

(52) U.S. Cl.
    CPC ........... *A61B 19/22* (2013.01); *A61B 19/2203* (2013.01); *A61B 2019/2211* (2013.01); *A61M 25/09* (2013.01); *Y10S 901/02* (2013.01)

(58) Field of Classification Search
    CPC ............ A61M 25/09; A61M 25/0905; A61M 25/09041; A61M 25/09116; A61B 5/6852; A61B 2017/1492; A61B 8/12; A61B 19/2203; A61B 2109/2211
    See application file for complete search history.

(56) References Cited

U.S. PATENT DOCUMENTS

| 4,944,727 | A  | * | 7/1990  | McCoy ......................... 604/528 |
| 5,349,964 | A  | * | 9/1994  | Imran et al. ................... 600/585 |
| 5,492,131 | A  | * | 2/1996  | Galel ............................ 600/585 |
| 7,544,170 | B2 | * | 6/2009  | Williams et al. ............. 600/585 |
| 7,713,190 | B2 | * | 5/2010  | Brock et al. .................. 600/114 |
| 8,790,297 | B2 | * | 7/2014  | Bromander et al. ........ 604/95.01 |
| 8,911,382 | B2 | * | 12/2014 | Hauck et al. .................. 600/585 |
| 8,961,433 | B2 | * | 2/2015  | Patel et al. .................... 600/585 |
| 8,974,408 | B2 | * | 3/2015  | Wallace et al. ............ 604/95.04 |
| 9,039,681 | B2 | * | 5/2015  | Wang et al. ....................... 606/1 |

* cited by examiner

*Primary Examiner* — Max Hindenburg
(74) *Attorney, Agent, or Firm* — Anderson Gorecki & Rouille LLP

(57) ABSTRACT

A method and apparatus providing precision external control of interventional medical procedures is presented. The apparatus includes a fixed frame, the fixed frame attachable to a patient and to a secure structure. The apparatus also includes a precision actuator in mechanical communication with the fixed frame, the actuator directing motion of a wire within a catheter or a catheter within the patient. Additionally the apparatus includes a control device in electrical communication with the actuator, wherein the control device controls the actuator.

15 Claims, 4 Drawing Sheets

PRECISION EXTERNAL CONTROL OF INTERVENTIONAL MEDICAL PROCEDURES

CROSS REFERENCE TO RELATED APPLICATIONS

The present application claims the benefit of U.S. Provisional Patent Application No. 61/742,246 filed on Aug. 3, 2012 which is incorporated herein by reference in its entirety.

BACKGROUND

A catheter is a thin tube extruded from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. Catheters can be inserted into a body cavity, duct, or vessel. Functionally, they allow drainage, administration of fluids or gases, access by surgical instruments, and also perform wide variety of other tasks depending on the type of catheter. The process of inserting a catheter is referred to as catheterization.

An embolism is the event of the lodging of an embolus (a detached intravascular mass capable of clogging a blood vessel at a site far from its origin) into a narrow blood vessel, which causes a blockage (vascular occlusion) in a distant part of the body.

SUMMARY

Physicians control the catheter during an interventional procedure by using their hands to perform a large variety of procedures. One such procedure is performing an extraction of an embolism. The conventional procedure of performing an extraction of an embolism during interventional radiological procedure is for the physician to hold a catheter with one hand and, with the other hand, pull on a wire (tension force) which protrudes from the catheter. Conventional mechanisms using catheters suffer from a variety of deficiencies including pulling with the precise amount of force for the precise amount of time. If not enough force is applied, the embolus will not be removed. If the force is applied too quickly, the embolus may break apart and cause further more distal emboli. If too much force is applied, then the blood vessel may be damaged. If the applied force is not correct or if the force is not applied over the appropriate amount of time, poor patient outcomes can result. This invention enables precision external control of a catheter(s) and wire(s).

Physicians controlling the catheter during an interventional procedure are present in the fluoroscopy room during the procedure. This exposes the physician to high levels of radiation. This invention enables controlled movement of the catheter(s) and wire(s) without requiring the physician(s) hands to manipulate the catheter(s) and wire(s); thus the physician can avoid high levels of radiation exposure.

Embodiments of the invention significantly overcome such deficiencies and provide mechanisms and techniques that provide precision external control of interventional medical procedures. The presently disclosed method and apparatus for precision external control of interventional medical procedures includes applying precise amounts of torque, compression, tension forces to a catheter in catheter-based procedures, such as is done by interventional radiologists, interventional neuroradiologists, vascular surgeons or interventional cardiologists. This is also applicable to other physicians may employ similar catheter based procedures. Examples in which this presently disclosed method and apparatus for precision external control of interventional medical procedures would be useful include, but are not limited to, embolectomy in the setting of an acute stroke, placement of coils into aneurysms, placement of stents into narrowed blood vessels and microcatheter work used in treatment of tumors. For the purposes of illustrating the technology/procedures, the procedure of extracting an embolism in the setting of an acute stroke will be described.

The present invention comprises a mechanism that applies torque, tension and compression in a measured fashion. The torque, compression, tension could be applied for a specified time period (e.g., 30 seconds). An example usage would be the removal on an embolism lodged in the brain. If the embolism is dislodged during this time period, the physician would continue with the removal of the embolism via standard medical procedures. If, however, the embolism were not dislodged during this initial period, the tension would be increased to the next level and the waiting time would be repeated. This process would be repeated i.e., sequentially increasing the tension and allowing time for this pulling pressure on the embolism to dislodge it.

In a particular embodiment the apparatus includes a fixed frame, the fixed frame attachable to a patient and to a secure structure such as a gurney frame, a wall or the like. The apparatus also includes a precision actuator in mechanical communication with the fixed frame, the actuator directing motion of a wire within a catheter or a catheter within the patient. Additionally the apparatus includes a control device in electrical communication with the actuator, wherein the control device controls the actuator.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
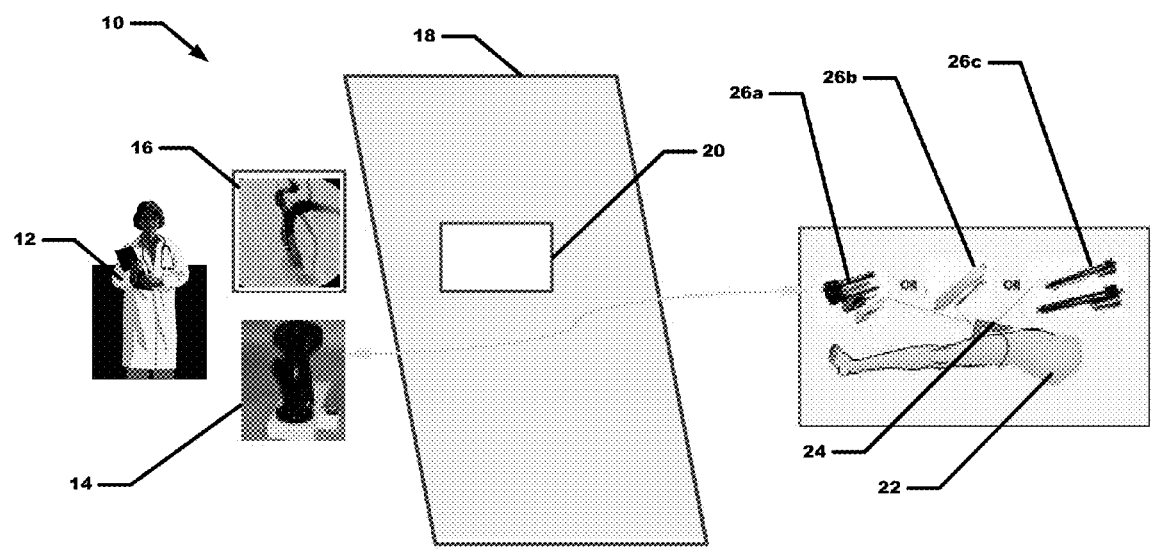
FIG. 1 shows an embodiment of a system for providing precision external control of interventional medical procedures in accordance with embodiments of the invention.

The embodiments set forth below represent the necessary information to enable those skilled in the art to practice the invention and illustrate the best mode of practicing embodiments of the invention. Upon reading the following description in light of the accompanying figures, those skilled in the art will understand the concepts of the invention and recognize applications of these concepts not particularly addressed herein. It should be understood that these concepts and applications fall within the scope of the disclosure and the accompanying claims.

The preferred embodiment of the invention will now be described with reference to the accompanying drawings. The invention may, however, be embodied in many different forms and should not be construed as limited to the embodiment set forth herein; rather, this embodiment is provided so that this disclosure will be thorough and complete, and will fully convey the scope of the invention to those skilled in the art. The terminology used in the detailed description of the particular embodiment illustrated in the accompanying drawings is not intended to be limiting of the invention. In the drawings, like numbers refer to like elements.

A method and apparatus is described which provides external control of a system for applying precise amounts of torque, compression, tension forces or shearing forces to the catheter and the wire inside of the catheter in catheter-based procedures, such as is done by interventional radiologists, interventional neuroradiologists, vascular surgeons or interventional cardiologists. This is also applicable to other physicians may employ similar catheter based procedures. Examples in which this patent would be useful include, but are not limited to embolectomy in the setting of an acute stroke, placement of coils into aneurysms, placement of stents into narrowed blood vessels, microcatheter work used in treatment of tumors.

The invention comprises an actuator system which is attached to a catheter and/or wire, and a control station for the physician to perform the medical procedure from outside of the operating room. Advantages include the physician being able to perform medical procedures external to the operating room and consequently not being exposed to radiation. An electronic control system is operated by the physician to provide precision tension, compression, torque and shearing forces applied to wire inside of the catheter and or to the catheter as well as variable speed/force for advancing of catheter.

Referring now to FIG. 1 a system 10 for providing precision external control of interventional medical procedures is shown. System 10 includes a fixed frame 24. The frame 24 is attachable to a patient and is also attachable to a bed frame, wall or ceiling for securing the patient in a fixed position. Also shown are different styles of precision actuators 26a, 26b and 26c. A single particular type of actuator would be used. The precision actuator is in mechanical communication with the fixed frame 24. The precision actuator is used for directing motion of a wire within a catheter or the catheter within the patient 22. System 10 further includes a control device 14 in electrical communication with the actuator, wherein the control device 14 controls the actuator.

FIG. 1 also shows a wall 18 separating the doctor 12 from the patient 22. Wall 18 includes shielding to protect the doctor from radiation. Wall 18 also includes a window 20 through which the doctor 12 can observe patient 22.

The doctor 12 has a high resolution monitor 16 which displays real time imagery of the patient and wire and catheter location within the patient. The doctor 12 uses control device 14 to provide signals to the actuator to provide forward and reverse movement of the wire at moderate speeds, to provide forward and reverse movement of the wire at slow speeds, to apply torque in clockwise or counter-clockwise directions and to provide other movement of the wire within the catheter.

Briefly, an example of the typical arrangement of the multiple coaxial catheters and wire are as follows: a first catheter enters the body of the patient through an extremity (e.g., a leg) and continues into the artery (in the case of entry into the leg, this would be the femoral artery.) This first catheter is nominally fixed to the extremity. A second catheter is placed inside of the first catheter and it protrudes out of the entrance of the first catheter and also extends into the artery. A third catheter is disposed inside of the second catheter and extends out of that catheter. The wire which follows an arterial path from the entry point to the embolism protrudes out of the third catheter.

Figure 2A:
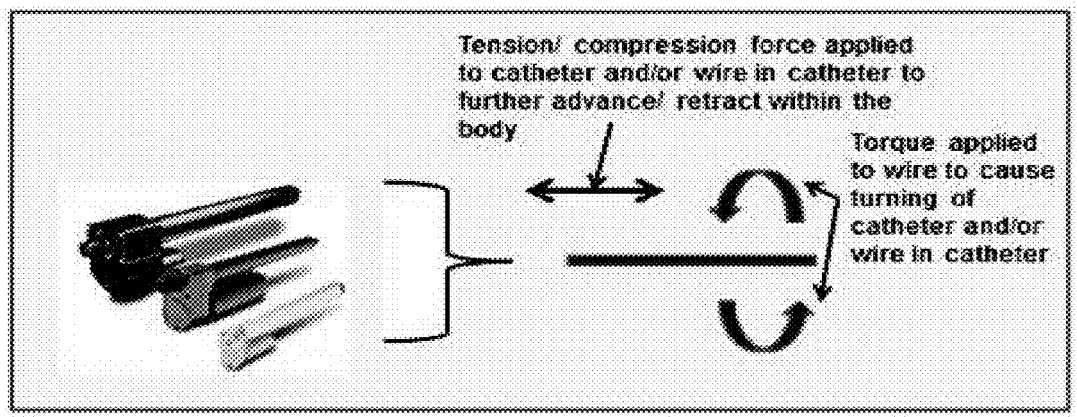
FIG. 2A shows an actuator and the resulting tension, compression, torque and shearing forces provided by the actuator in accordance with embodiments of the invention.
Figure 2B:
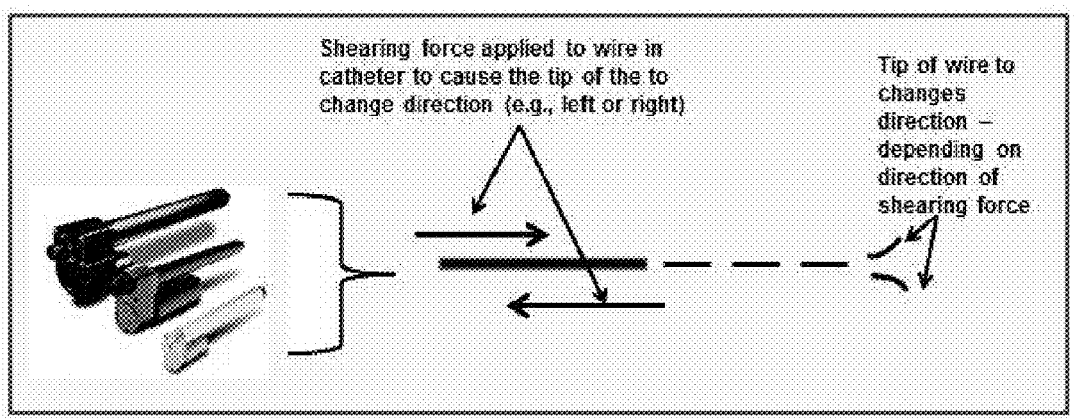
FIG. 2B shows an actuator and the resulting shearing forces provided by the actuator in accordance with embodiments of the invention.

The example devices 26a, 26b, and 26c shown are precision actuators which are fixed to a catheter, nominally using a clamp. The wire that extends from the catheter to the embolism extends through the catheter(s). The device contains a second clamp which is affixed to the wire. This second clamp is integral to the application of torque, compression, tension or shearing force provision portion of the device. In some embodiments a dial is used which would show the current level of tension being applied to the wire and may further include a timer to indicate the period of time the indicated tension has been applied. Each time that a new level of tension is applied, the timer is reset. FIG. 2A shows a linear actuator which can be used to provide tension and compression to the wire or catheter and also provide torque to the wire or catheter. As shown in FIG. 2B, the actuator can be controlled to provide a shearing force to cause the tip of the wire to change direction.

In some embodiments a tension bar 26b is used to sequentially apply tension to the wire as the lever arm is rotated. The tension bar 26b would be calibrated and differing levels of tension values would be inscribed on the lever arm. This instantiation would be mechanical in nature and the physician would change the levels of torque for each iteration of increasing tension was applied until the embolism was dislodged. In other embodiments an internal clamp, which is applied to the wire would be affixed to an internally rotating bracket, which when rotated clockwise would apply compression forces to the wire and when rotated counterclockwise, apply tension forces to the wire. This instantiation would be amenable to the display described above.

The next major component is an actuator system which controls whichever of the above or similar devices which enable application of tension, compression, or torque. It is in essence a robotic arm with an additional feature of variable speed advancement of the third catheter. (Note: the initial placement of the catheters would be performed by the physician in the operating room, prior to application of high levels of radiation energy.) The actuator system would be attached to a stable element such as to a rail on the gurney. The actuator system would include a processor and an electronic link to the physician control station.

The final component is the physician control station. Manual dials/control levers would be moved in the desired direction to apply tension, compression, or torque. A control dial (small circular wheel) would control the variable speed of advancement of the third catheter. A display would indicate tension, compression, and torque pressures and also the duration these pressures have been applied. A large high resolution display would show the latest position of the catheters, wires, etc., as would normally be viewed by the physician, if he were located inside of the operating room.

Figure 3:
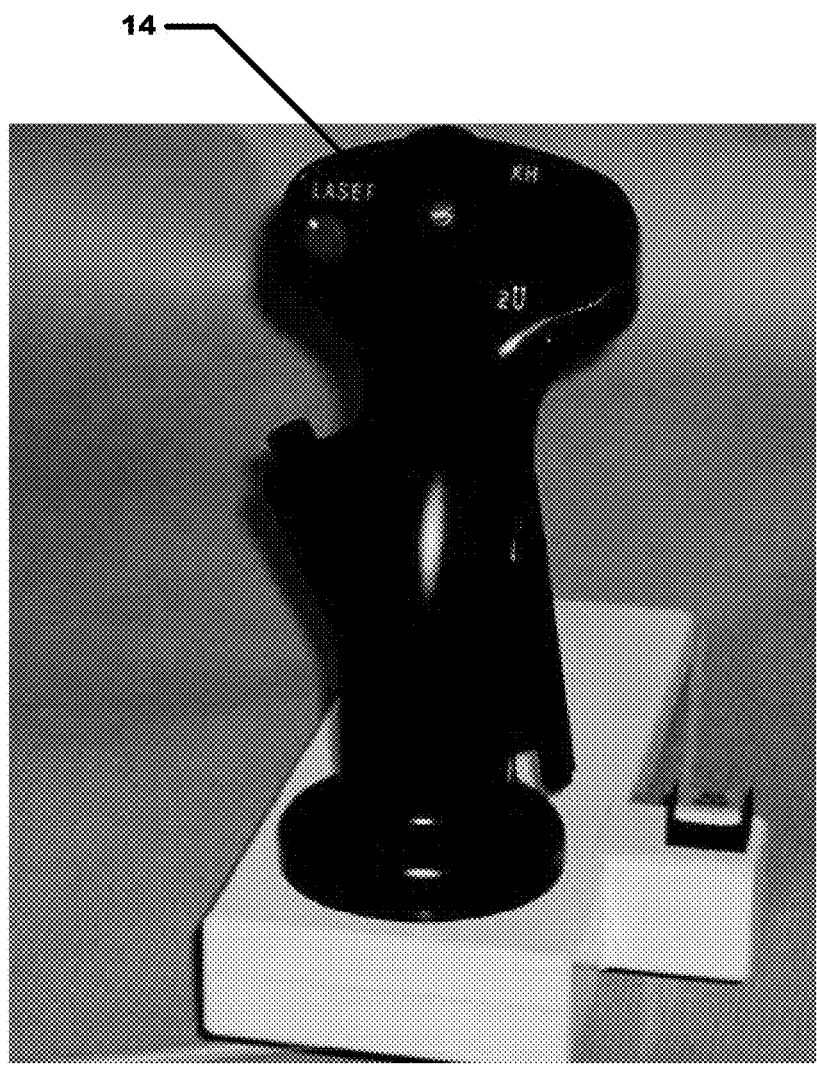
FIG. 3 shows an example control device that is used to control a wire or a catheter in an operation specific apparatus in accordance with embodiments of the invention.

Referring now to FIG. 3 a view of a particular type of control device 14 is shown. While a joy-stick type device is shown here, it should be appreciated that other types of control devices as would be known to one of ordinary skill in the art may also be employed. While the control device here is also a wireless device, it should be appreciated that the invention is not limited to wireless control devices, and that wired devices may also be used. The control device 14 has a variety of knobs, buttons, and motion detection circuits that translate commands from the doctor to an actuator. The doctor is able to use the control device 14 to define precise movements of the wire or catheter within the patient.

Figure 4:
FIG. 4 shows an image as seen by medical doctor as the doctor guides the wire to a specific location for needed surgery in accordance with embodiments of the invention.

FIG. 4 depicts a display 16 showing a radiology picture the medical doctor views during the conduct of the operation. The doctor uses this imagery as the basis for the control of the wire and any special apparatus during the conduct of the operation.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Accordingly, it is submitted that that the invention should not be limited to the described embodiments but rather should be limited only by the spirit and scope of the appended claims.

What is claimed is:

1. An apparatus comprising:
   a fixed frame, said fixed frame attachable to a patient and to a secure structure;
   a precision actuator in mechanical communication with said fixed frame, said actuator directing motion of a wire within a catheter within said patient or a catheter within said patient, wherein said actuator comprises a tension bar; and
   a control device in electrical communication with said actuator, wherein said control device controls said actuator.

2. The apparatus of claim 1 wherein said control device controls at least one of forward movement of said wire within said catheter or said catheter and reverse movement of said wire within said catheter or said catheter.

3. The apparatus of claim 1 wherein said control device controls at least one of clockwise torque of said wire within said catheter and counter-clockwise torque of said wire within said catheter.

4. The apparatus of claim 3 wherein said torque comprises a time-based application of torque.

5. The apparatus of claim 1 wherein said control device controls compression of said wire within said catheter.

6. The apparatus of claim 5 wherein said compression comprises a time-based application of compression.

7. The apparatus of claim 1 wherein said control device controls tension of said wire within said catheter.

8. The apparatus of claim 7 wherein said tension comprises a time-based application of tension.

9. The apparatus of claim 1 wherein said control device controls a shearing force of said wire within said catheter.

10. The apparatus of claim 1 wherein said fixed frame, said actuator and said control device are used to extract an embolism.

11. The apparatus of claim 1 wherein said actuator provides variable mechanical advantage.

12. The apparatus of claim 1 wherein said control device communicates with said actuator via a wireless link.

13. The apparatus of claim 1 wherein said tension bar is used to sequentially apply tension to the wire as a lever arm is rotated.

14. The apparatus of claim 13 wherein said tension bar is calibrated and differing levels of tension values are inscribed on the lever arm.

15. The apparatus of claim 13 wherein a physician would change the levels of torque for each iteration of increasing tension was applied until an embolism is dislodged.

* * * * *